United States Patent [19]

Turner et al.

[11] Patent Number: 4,974,587
[45] Date of Patent: Dec. 4, 1990

[54] APPLICATOR ARRAY AND POSITIONING SYSTEM FOR HYPERTHERMIA

[75] Inventors: Paul F. Turner, North Salt Lake; Victor A. Vaguine, Salt Lake City, both of Utah

[73] Assignee: BSD Medical Corporation, Salt Lake City, Utah

[21] Appl. No.: 288,414

[22] Filed: Dec. 22, 1988

[51] Int. Cl.[5] ............................. A61F 7/00; A61N 5/00
[52] U.S. Cl. ..................................... 128/399; 128/804; 128/402
[58] Field of Search ............... 128/399, 400, 401, 402, 128/783, 798, 802, 804; 600/2, 10, 15

[56] References Cited

U.S. PATENT DOCUMENTS

| 4,140,130 | 2/1979 | Stom, III | 128/400 |
| 4,190,053 | 2/1980 | Sterzer | 128/399 |
| 4,397,313 | 8/1983 | Vaguine | 128/401 |
| 4,397,314 | 8/1983 | Vaguine | 128/399 |
| 4,690,156 | 9/1987 | Kikuchi et al. | 128/804 |
| 4,692,980 | 6/1987 | Turner | 128/804 |
| 4,699,475 | 6/1987 | Turner | 128/399 |
| 4,712,559 | 12/1987 | Turner | 128/399 |

FOREIGN PATENT DOCUMENTS

| 0194897 | 9/1986 | European Pat. Off. | 128/400 |
| 0249532 | 12/1987 | European Pat. Off. | 128/804 |
| 0251746 | 1/1988 | European Pat. Off. | 128/804 |
| 2135891 | 9/1984 | United Kingdom | 128/804 |
| 2151489 | 7/1985 | United Kingdom | 128/804 |

Primary Examiner—Edward M. Coven
Assistant Examiner—Jessica J. Harrison
Attorney, Agent, or Firm—Mallinckrodt & Mallinckrodt

[57] ABSTRACT

The use of an externally located dipole array mounted upon a high dielectric material for heating biological tissues is disclosed. This dipole array provides improved flexibility and adaptability to varying tissue surface contours. The adjustable dipole antenna array or other type of electromagnetic antenna applicators provides an ability to adapt the heating pattern to meet the needs of the different tissue zones, applicator positions, and applicator mechanical scanning by adjusting individual power amplitude and phase to the various elements of the applicator array for controlling the heat distribution of heat in target tissue having areas of varying power absorption and cooling effect (blood flow). The array design may also include capacitively coupled metal elements in the form of strips, patches or tubes. The electromagnetic heating elements are attached to a transparent flexible dielectric fluid filled envelope, tube, or bag for viewing both the tissue surface being heated and positioning the applicators and temperature sensors. The flexibility of this array provides uniform heating of a diversity of surface contours. Also, an electromechanical positioning system for the applications allows the applicators to be selectively positioned in the tubes, and thereafter repositioned during treatment.

22 Claims, 4 Drawing Sheets

APPLICATOR ARRAY AND POSITIONING SYSTEM FOR HYPERTHERMIA

This invention relates to hyperthermia systems and more particularly to an improved system for treating tissues having contoured surfaces and varying power absorption and cooling effects.

BACKGROUND OF THE INVENTION

The use of electromagnetic (EM) energy in the heating arts has been utilized for many years. In recent years EM energy has been utilized in diathermy and hyperthermia to provide therapeutic heating to diseased tissue.

The use of heating for cancer therapy is commonly called hyperthermia which is one of the intended uses of this invention. This may be in combination therapies with other treatments such as surgery, ionizing radiation, and chemotherapy. In such treatments it is common to attempt heating the diseased tissue to above 42 degrees C., but often undesirable complications occur when the maximum tissue temperature exceeds 45 to 46 degrees C. Some of these complications include damage to healthy normal tissue, ulceration, and higher incidence of surface blisters and burns The application of the frequencies used have typically ranged from 100 KHz to 2450 MHz.

A recently popular practice has been the use of coaxial dipole radiators of very small cross-sectional size which were inserted directly into the tissue through implanted catheters. This method has enabled a great deal of flexibility for the therapist to position the heating applicators at the location of the diseased tissue only. The method has been called interstitial hyperthermia. The most common types of interstitial are the microwave interstitial (MI) and local current fields (LCF). The microwave interstitial array methods utilizing synchronous fields at the same frequency was first disclosed in U.S. Pat. No 4,448,198. This method and system used several microwave interstitial dipole antennae which were placed within interstitially placed catheters. This type of array could utilize many antennae, but were constrained to be placed along a circular circumference so as to surround a target zone The synchronous operation of each applicator with the same or fixed relative phase would provide substantially improved heating in the tissues within the central zone of the array. This method did not include arrays of these antennae placed along a straight or partially curved line This method did disclose the use of phase shifters to modify the phase of each antenna. One method to accomplish this phase shift was the use of motorized positioning systems under computer control to move and position the antenna coaxial cable.

U.S. Pat. No. 4,669,475 issued June 2, 1987 discloses the same system modified with improved antennae designs to provide tip heating and contain integral thermometry sensors within the antenna heating tip area. This patent also disclosed the use of independent phase and amplitude steering to control the heating zone. This method and equipment was also exclusively described as an internal or interstitial use of these small dipole antenna.

Another system is known using centrally placed dipole antennae in the central zone of such arrays. These central antennae accomplish a partially destructive interference of the central energy focus which is often too hot. This method also utilizes microwave interstitial arrays which are placed into catheters which are in dwelling within the tissues to be heated (U.S Patent Application Serial No. 161,456, BSDM B5578).

Other U.S. patent prior art which have been cited relevant in similar applications are Hansjurgens U.S Pat. No. 3,774,620, Leveen U.S. Pat. No. 4,095,602 Wyss et al., U.S. Pat. No. 4,148,321, Armitage U.S. Pat. No. 4,285,346, Gammell U.S. Pat. No. 4,346,715, Sterzer U.S. Pat. No. 4,190,053, Paglione U.S. Pat. No. 4,204,549, Sterzer U.S. Pat. No. 4,311,154, Brisson U.S. Pat. No. 4,322,594, Vaguine U.S. Pat. No. 4,397,313, and U.S. Pat. No. 4,397,314, Cosman U.S. Pat. No. 4,411,874, and Whalley U.S. Pat. No. 4,237,898.

Another method and device uses capacitive coupling to transfer lower frequencies such as 1 to 100 MHz through an in-dwelling catheter into the tissue to be heated. This design relies upon capacitive applicators acting as electrodes. That is, they operate in pairs having opposite voltage polarities, or they work with a larger metal plate or structure to act as the opposite polarity electrode. In this way high frequency currents are made to flow between these opposing polarity structures and though the intervening tissue, thereby heating the tissue. These antennae were described as being completely within tissue to be heated (U.S. Pat. No. 4,712,559 issued Dec. 15, 1987).

The use of electromagnetic heating has also been applied externally to the tissue surface through either tissue contacting or noncontacting applicators. These have most commonly been in the form of metallic capacitive plates or microwave antenna (usually in the form of waveguides). The problem with these two external methods is that except for the intensity of the heating field, the heating distribution is not controllable Thus, these common techniques often result in poor heating of substantial portions of diseased tissue or in excessive heating of tissues.

In an effort to more fully provide flexibility for deep heating target tissue zones, a device was developed and described in U.S. Pat. No. 4,462,412 issued July 31, 1984. This system includes an annular phased array device which was a rigid array of 16 external applicators of the waveguide form which surrounded the body in a cylindrical or annular manner. This also included the use of a high dielectric fluid such as water to fill the area between the applicators and the tissue surface. Such annular phased array device is capable of providing selective and deep hyperthermia and utilizes the phase and power amplitude steering of EM energy. The selection of frequency was related to the diameter of the tissue cross-section which was to be deeply heated. This device did not claim any particular advantages in the heating or treatment of surface or superficial disease sites. The selection of the frequencies to achieve deep heating force the frequencies to be quite low which resulted in very large wavelengths These wavelengths were typically 30 cm long within the high water tissues of the body. The control of energy could not easily be confined to zones smaller than $\frac{1}{3}$ to $\frac{1}{2}$ of the wavelength within the tissue. Thus, the problem with this system is that it provides fairly poor heating control for superficial treatments where the heating pattern would need to be adapted to locally different heating and cooling effects.

A similar but more advanced cylindrical annular phased array device is disclosed in U.S. Pat. No. 4,589,423, issued May 20, 1986. This device is similar to the first annular array patent, but uses external dipoles in a phased array approach This design is intended to provide deep and central tissue heating by surrounding the target tissue zone with energy from all surface sides to maximize the delivery of energy at a particular deep zone. This design utilizes several external dipole antennae along the perimeter of a high dielectric annular envelope called a bolus which separated the dipoles from the tissue surface. A problem with known devices using boluses is that they prevent viewing the tissue surface during heating and the positioning of the applicators and temperature sensors. In this device again the frequencies used to achieve deep heating are so low that control of heating selectively along the surface and subsurface tissues is a problem. The typical frequency described for a 20 to 30 cm diameter tissue regions was 100 MHz. This frequency provided a 27 cm wavelength within the high water tissues. Selective alteration of the heating field was not very precise along the surface zones. This design was also described in detail in a published article by Turner entitled "Mini-Annular Phased Array for Limb Hyperthermia", IEEE Trans. on MTT, Vol. MTT-34, No. 5, pp. 508-513, May 1986.

Another approach was published by Sterzer et al. entitled "RF Therapy for Malignancy", IEEE Spectrum, December 1980, pp. 32-37. This article described a very high frequency array of micro-strip dipole antennae mounted on a ridged dielectric substrate where a dielectric powder (bean-bag) was placed between the antennae and the tissue surface. The described operating frequency was 2450 MHz. This device did not contain any provisions for altering the power amplitude or phase of the radiating antennae. Thus, little practical clinical use has been made of this design because of its inflexibility to adapt its heating to the requirements of the tissue being heated.

A further problem with known hyperthermia devices using applicators containing tubes is that electromechanical positioning means have not been included for selectively positioning the applicators in the tubes for and during treatment.

SUMMARY OF THE INVENTION

Accordingly it is an object of the hyperthermia device of this invention to avoid overheating or underheating of diseased tissue during hyperthermia treatment.

Another object of the hyperthermia device of this invention is to provide a noninvasive device having improved adaptability for treating tissues having varying surface contours.

Yet another object of the invention is to provide a hyperthermia device providing visual viewing of the tissue surface being heated and the location of the applicators and temperature sensors.

A further object of the invention is to provide a hyperthermia device in which the position of the applicators are selectively positionable for and during treatment.

Briefly stated the hyperthermia device of this invention includes an array of electromagnetic (EM) energy noninvasive applicators electromechanically mounted for adjustment in tubes The tubes are attached to a transparent bolus allowing good thermal contact with contoured tissue surfaces and viewing of the tissue surface and location of the applicators with respect to the contoured tissue surfaces for individual adjustment of phase, power, and location within the tube for producing a heating pattern meeting the needs of different tissue zones.

BRIEF DESCRIPTION OF THE DRAWINGS

Other objects and features of the invention will become more readily apparent from the following detailed description when read in conjunction with the drawings in which.

DESCRIPTION OF THE PREFERRED EMBODIMENTS

Figure 1:
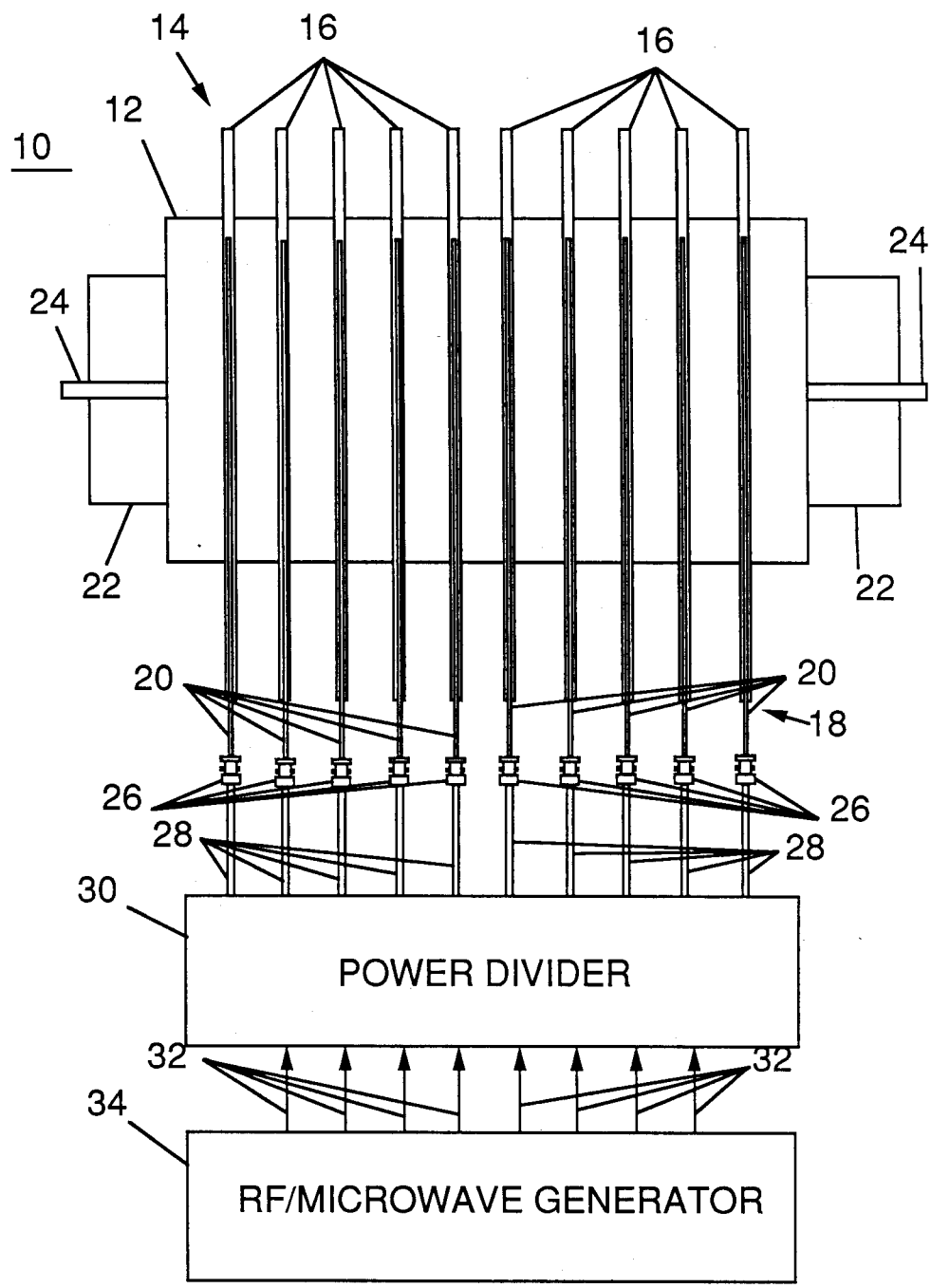
FIG. 1 is an elevational view of the hyperthermia device of this invention including a block schematic of the device circuit.

FIG. 1 shows the hyperthermia applicator array and positioning system diagram 10 which shows the dielectric envelope or bag 12, hereafter called the bolus, which has attached to a side wall, either inside or outside of the thin dielectric bolus membrane wall, an array 14 of dielectric tubes, sleeves, or catheters 16. These tubes 16 provide an insertion pathway for an array 18 of small diameter electromagnetic EM energy applicators 20. The tubes 16 are functionally attached to the bolus 12 membrane wall in a parallel fashion to each other as shown. These tubes 16 therefore provide an insertion, positioning and holding means for the parallel placement of the long EM applicators 20. The bolus 12 is attached to the surface adjacent to the area to be heated by straps of flaps 22 which could be in the form of a belt or strap. The bolus bag 12, for example, is a transparent, flexible, plastic bag filled with a high dielectric fluid, such as deionized water, through tubes 24. The tubes 24 also enable the circulation of fluids through the bolus 12 by selecting one as a fluid filling tube and the other as the fluid exit tube. The applicators 20 are attached through coaxial connectors 26 to system coaxial cables 28. The coaxial cables 28 are connected to a power divider circuit 30. The power divider circuit 30 is connected through channels 32 to an R/F microwave generator 34. The power divider circuit provides a division of EM power to heat all of the applicators required for a particular heating field size. It is at times necessary to provide this capability of power division when the number of applicators needed exceed the number of independent power channels 32 provided by the EM power generator 34.

FIG. 1 shows that for an 8 channel generator that ten or more outputs 28 may be needed. Thus, some of the power channels provide a division of channel power to supply more applicators than the number of generator channels These power channels are independently controllable to provide various heating pattern effects. The generator parameters which can be usefully altered to accomplish desirable heating pattern improvements are channel power, phase, and frequency. It is also an important part of this system that the insertion position of the applicators 20 may be altered by differing or changing the insertion position of each or some cf the applicators 20 before or during actual heating. If such is done during actual heating, it is necessary to provide a form of amplitude modulation or variation which is synchronized with the applicator positions. These functions are either manually performed or made part of a control panel or mini-computer.

Figure 2:
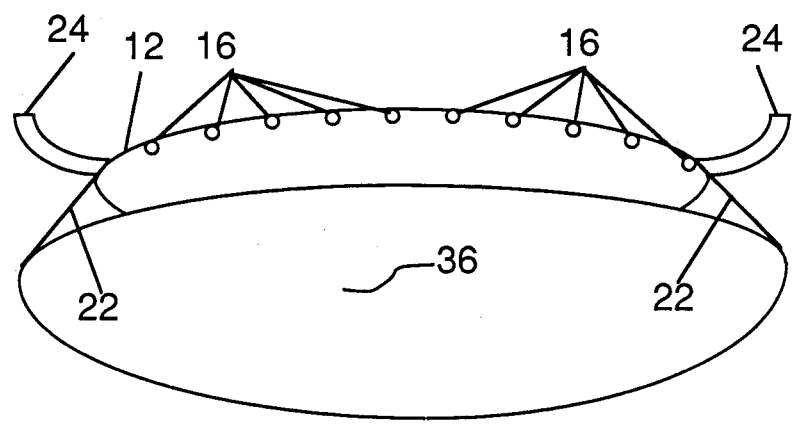
FIG. 2 is a partial isometric view of the hyperthermia device of this invention.

FIG. 2 shows another view of the system. This view shows the bolus 12 and tubes 16 for the insertion of the applicators overlying the zone to be heated 36. The view is the plane perpendicular to the tubes 16 long direction. As can be seen, the tubes 16 are somewhat displaced from the surface of the target zone 36 by the bolus thickness resulting from the partial fluid filling of the closed bolus bag. The straps 22 are used to secure the placement of the bolus bag 12 to the surface adjacent to the area to be heated.

Figure 3:
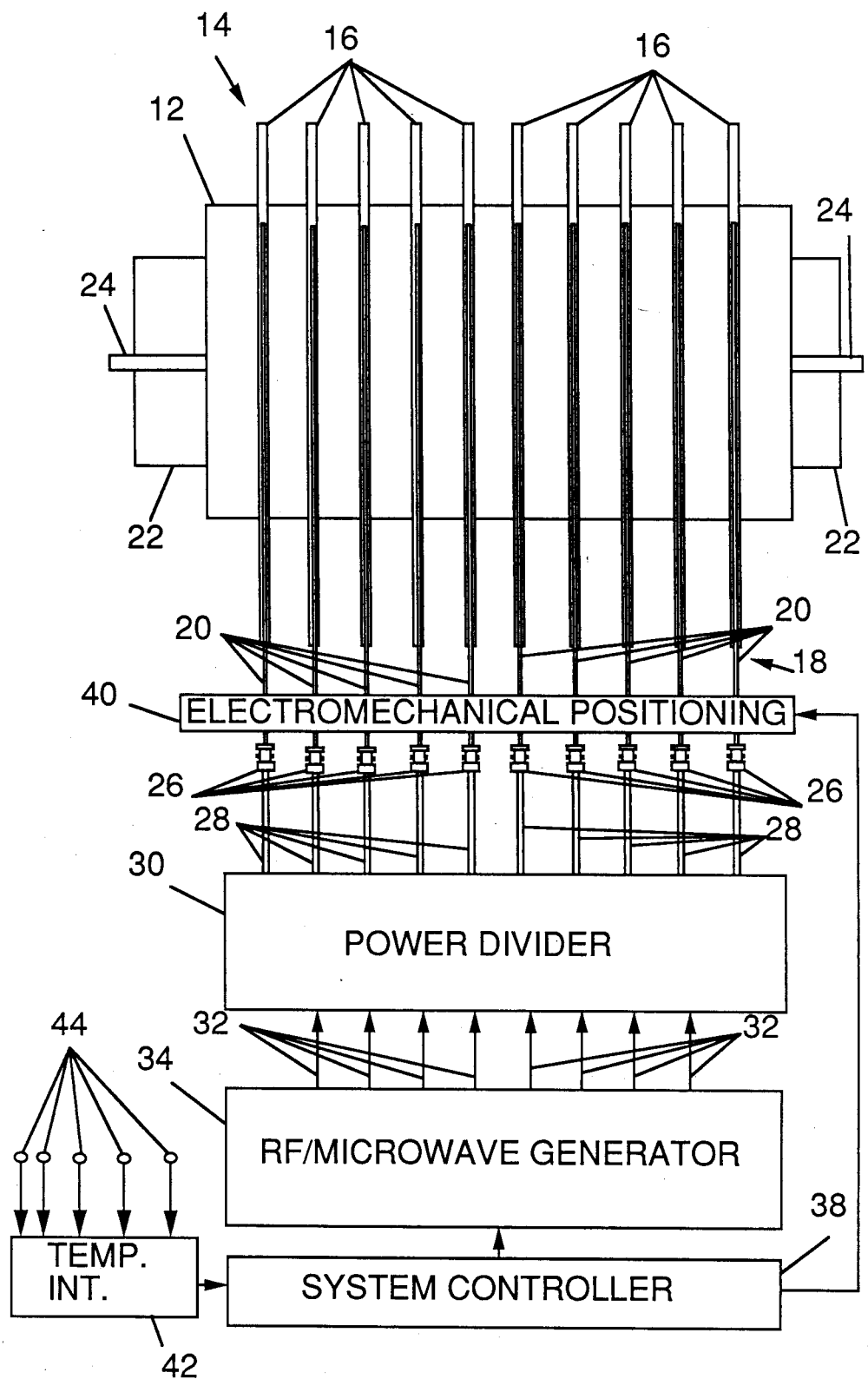
FIG. 3 is an elevational view of a second embodiment of the hyperthermia device of this invention.

FIG. 3 shows an alternate form of the system shown in FIG. 1 in which a system controller 38, an electromechanical positioning unit 40, a temperature interface unit 42, and several temperature sensors 44 have been added. The system controller 38 function is to control the setting of the generator channels power, phase, and frequency. The controller also controls the electromechanical positioning unit 40 for proper insertion position of the applicators 20 within the tubes 16 to improve the control of the heating field. The positioning of these applicators provides an increased length of heating for each applicator 20. This mechanical positioning is accomplished by a motorized electromechanical positioner 40. The motorized electromechanical positioner 40 structure is, for example, that of the thermal sensor locating means shown in FIG. 10 of and described in U.S Pat. No. 4,672,980, issued June 16, 1987. Briefly stated the structure includes two capstan rollers in contact with a sheave 92 amongst which the coaxial cables of the applicators pass. The sheave is driven by stepping motor or other means which allows the applicator position to be varied in the tube 16 by the controller to precisely position each applicator. Thus, this positioner 40 can alter the position of the applicators by either individual positioning or by synchronous positioning movements of all or a part of the applicators 20 within the tubes 16. The controller 38 controls all these parameters, so it provides coordinated adjustments in applicator position and the selection of power level, phase, and frequency. The temperature sensors 44 are in contact with or attached to the surface or within the tissue of the area to be heated. This provides through the temperature interface 42 a means to inform the controller 38 of the temperature in several zones within the tissue 36 being heated. If the controller contains the information about the position of each temperature sensor, it can thereby provide individual control of the generator parameters to each channel to improve the heating uniformity as indicated by the temperature sensors 44. Normally, it would be the channel power which would be altered to increase or decrease the tissue heating indicated by the sensors 44 in the nearest tissue zone monitored underlying the applicators powered by the channel 32 being altered. This would best be done by a mini-computer contained within the controller 38 so that these temperature measurements and power adjustments can be rapidly and automatically controlled within the system controller 38.

The applicators 20 can be either microwave antennae or LCF capacitance type electrodes. The possible microwave antennae designs suitable are coaxial dipole, monopole, helical spiral, helical coil, leaky coaxial line, split coax line, metal strip dipoles, and stepped diameter collar coaxial sections. All these create a dominant electric field to be in line with the long axis of the applicator EM radiated field. At times it may be useful to alter the radiated phase of some of the coaxial microwave antennae to create zones of partial destructive interference, thus moderating what may be otherwise an undesirably hot area. These phase adjustments would normally be done with the aid of computer calculations to determine the overall effect by such a phase cancelling effect as described in U.S Patent Application Serial No. 161,456, BSDM B5578.

The conformable adaption of these microwave coaxial antennae to the displaced position along the surface of a high dielectric bolus provides application flexibility. This enables a therapist to adapt the heating field size to be applied to the diseased tissue area. This type of bolus is very flexible and automatically conforms with the non-smooth contours typical of many diseased tissues such as cancerous tissues. This conformable shaping of the high dielectric bolus and the antennae array provides more uniform transfer of EM energy into the tissue as well as better surface temperature control by the substantially steady fluid temperature within the bolus. Normally, the bolus fluid should not be a material which is directly heated by the EM field. Deionized water is an excellent example of a fluid which does not heat up substantially as does the biological tissue in the presence of EM fields Also such water is a very high dielectric material with relative dielectric constant of 78.5. Air has a relative dielectric constant of 1. The use of this very high dielectric fluid has the effect of selectively channeling the radiated EM energy from each antenna to the tissue to be heated. The energy does not significantly transfer to the air space just outside the bolus, because the design of the antenna radiating segments are so short that efficient radiation only occurs within the very high dielectric media such as water and tissue. This is because the wavelengths within the high dielectrics are very short compared to air, enabling more efficient radiation. Also the characteristic impedance of air is well known to be 377 ohms per square Deionized water has a characteristic impedance of about 40 ohms per square. As energy is directed from the microwave antennae, the air region would present a 377 ohms per square load in parallel with the bolus load of 40 ohms per square This effect alone would result in about 10 times more power being transferred through the water filled bolus than the air outside. An additional effect is the lower efficiency of the short antennae to the air zone. Thus, efficient energy transfer is provided without the need of additional shielding material outside the bolus space. This enables the bolus to be made transparent in the preferred configuration to allow viewing of the surface being treated to improve safety and visual monitoring to avoid excessive heating of the surface tissues within the heating field. Common opaque applicators have caused surface blisters or burns in about 8 to 10 percent of the cancer patients treated with hyperthermia. Many of these complications were observable as soon as the applicator was moved away from the treatment field. Thus, if the applicators were transparent it would enable a therapist to observe the reddening of the tissues which commonly occurs prior to the formation of a heat blister or burn and intercede to prevent excessive heating of that zone. The control system would also be able to adapt the power delivered to each zone to compensate for the differential blood flow which would likely occur within different regions of the heating field.

Figure 4:
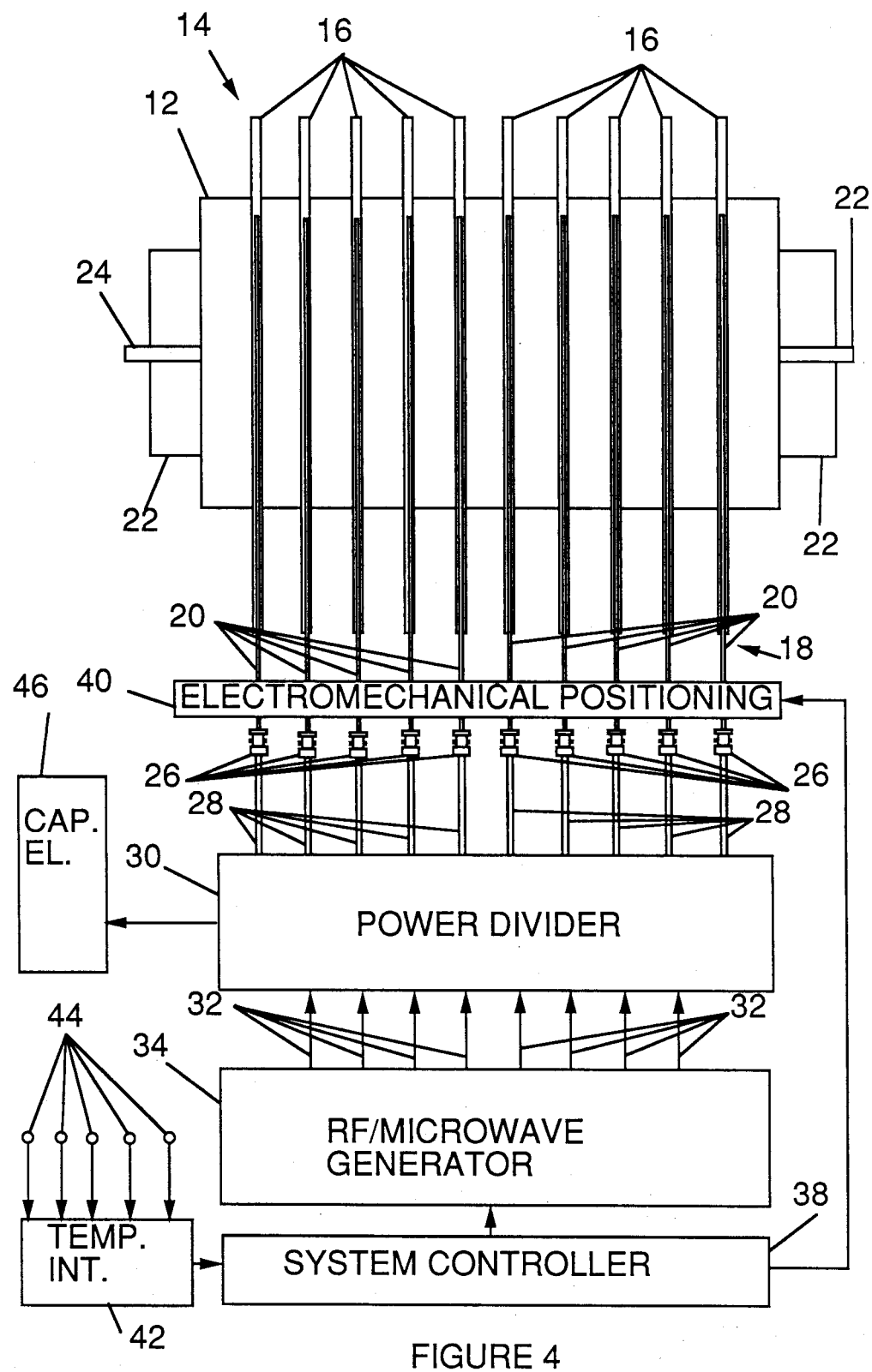
FIG. 4 is an elevational view of a third embodiment of the invention.

FIG. 4 is an alternative form of the system shown in FIG. 3. In FIG. 4 the applicators 20 utilized are LCF or capacitive electrode probes. This means that each applicator acts as an electrical source electrode of alternating voltage causing an alternating current to flow away from the applicator 20 to an oppositely polarized voltage electrode. This embodiment requires either an additional element 46 of an electrode or a second electrode applicator array oriented at another area of the tissue located, for example, on an opposing tissue surface. When the array of electrodes are all at essentially the same voltage phase but opposite in phase of the opposing electrode 46, than currents flow away from the applicators 20 in a perpendicular path. The perpendicular path is also the path of the electric field with the heated tissue. This is opposite in direction of the electric current induced in the tissue from the microwave antennae which is aligned with the long directions of the applicator shaft.

The operation of the system controller 38, electromechanical positioning element 40, temperature interface 42, and temperature sensor probes 44 is the same as described for FIG. 3. However the power divider in this case would be providing a return current path for each of the capacitive electrode applicators 20. The power divider would normally also, require an integral impedance tuner which would be used to maximize the transfer of energy between the capacitive electrode and the tissue. The return current electrode 46 and the tissue path would be the path of this tuning circuit as is common with LCF electrode methods in interstitial applications. The preferred operational frequency would be from 1 to 100 MHz as described in U.S. Pat. No. 4,712,559 issued Dec. 15 1987.

The controller is capable of controlling the position of the electrodes and the power, phase, and frequency of the EM energy from the multiple channel generator. As described in the interstitial electrode prior art, the lengths of the enlarged diameter metal collars used to selectively transfer the energy (below microwave frequencies) into the tissue, would enable a significant degree of selectivity in the electrode heating length. Although the use of this concept has been disclosed for the interstitial electrode arrays, its use is extended herewith in connecting external applicator arrays separated by a fluid bolus such as water. In the case of the electrode array heating only, it is suitable to utilize a concentrated saline solution if desired within the bolus space. Such a conductive media acts to channel the conduction currents as well as the capacitively coupled currents to the tissue. When a deionized water bolus is used in the LCF electrode array, it is only the capacitive currents or charge displacement currents which are transferred through the bolus. Salt water is not normally a suitable bolus for the microwave arrays because most of the power would be absorbed and converted to heat within the saline bolus since it is actually radiated through the bolus. The LCF capacitive electrode system of FIG. 4 would not substantially heat a very conductive salt water bolus since the currents would flow in series through a very conductive bolus into a less conductive tissue region toward the other electrode 46. This would therefore impart more heating to the tissue than to the conductive bolus Low heating would also be transferred into the deionized water bolus with the system of FIG. 4.

The use of the electromechanical positioning system to also position the temperature sensors is included in the above mentioned U.S. Pat. No. 4,672,980.

Although several embodiments of this invention have been described, it will be apparent to a person skilled in the art that various modifications to the details of construction shown and described may be made without departing from the scope of the invention.

What is claimed is:

1. An apparatus for hyperthermic treatment comprising:
    a transparent, flexible means containing a dielectric fluid with a dielectric constant of at least 2, and walls forming a plurality of tubes for applicators of an array of applicators, said transparent, flexible means allowing good thermal contact with contoured tissue surfaces and viewing of the heated tissue surface to anticipate tissue burning and proper treatment location of the array of applicators;
    an array of applicators, each applicator thereof adjustably mounted in a tube of the plurality of tubes;
    an electromechanical positioning means including means connected to each applicator for selectively adjusting the position of each applicator in its corresponding tube;
    a power divider means having a plurality of output ports connected to the applicators of the array of applicators for supplying power thereto at selected phase, amplitude, and frequency;
    an RF/microwave generator means connected to the power divider means for supplying power having a selected phase, amplitude and frequency thereto for distribution; and
    a controller means connected to the RF/microwave generator means for controlling the phase, amplitude, and frequency output thereof, and to the electromechanical positioning means for selectively adjusting the positions of the applicators of the array of applicators within the tubes of the plurality of tubes for producing a heating pattern meeting the needs of different tissue zones.

2. An apparatus for hyperthermic treatment according to claim 1 further including a tissue temperature sensing means for generating tissue temperature indicating signals, and wherein the controller means is connected to the temperature sensing means and responsive to the tissue temperature indicating signals for controlling the power output of the RF/microwave generator means.

3. An apparatus for hyperthermic treatment, comprising:
    a plurality of electromagnetic energy applicators;
    a power distribution means for distributing electromagnetic power to the plurality of electromagnetic energy applicators;
    a flexible support means providing good thermal contact with a contoured tissue surface when the support means is placed against such contoured tissue surface; and
    a plurality of applicator receiving sites formed in association with the support means, each applicator receiving site being configured to receive and hold at least one electromagnetic energy applicator, whereby the plurality of electromagnetic energy applicators are positioned at selective receiving sites to form an array of electromagnetic energy applicators to provide electromagnetic energy through the flexible support means to a tissue target to heat such tissue target.

4. An apparatus for hyperthermic treatment according to claim 3 wherein the flexible support means includes a transparent, flexible, plastic bag, and a fluid contained within the bag.

5. An apparatus for hyperthermic treatment according to claim 4 wherein the transparent, flexible, plastic bag includes walls forming a plurality of tubes for providing an insertion, positioning and holding means for the parallel placement of the applicators of the array of applicators.

6. An apparatus for hyperthermic treatment according to claim 5 wherein the transparent, flexible, plastic bag further includes a fastener means for attaching the bag to a surface to be heated.

7. An apparatus for hyperthermic treatment according to claim 5 further including the positions of the applicators within the plurality of tubes.

8. An apparatus for hyperthermic treatment according to claim 3 wherein the power distribution means includes a controller means connected to an RF/microwave generator for controlling the phase, amplitude and frequency of the generator power output, an RF/microwave generator connected to the system controller and responsive to commands issued by the controller for outputting power having a preselected phase, amplitude, and frequency, and a power divider connected to the RF microwave generator for dividing the power for a plurality of power channels connected to the array of applicators.

9. An apparatus for hyperthermic treatment according to claim 8 further including a plurality of tissue temperature sensors, a temperature interface means connected to the plurality of temperature sensors for receiving temperature indicating signals and multiplexing the temperature indicating signals to the controller means, said controller means operative responsive to the temperature indicating signals for adjusting the power amplitude output of the RF/microwave generator.

10. An apparatus for hyperthermic treatment according to claim 3, wherein the flexible support means is transparent to allow viewing of the surface of the tissue over which the support means is placed.

11. An apparatus for hyperthermic treatment according to claim 3, wherein the flexible support means includes fastening means for fastening the flexible support means over a tissue surface.

12. An apparatus for hyperthermic treatment according to claim 3, further including an electromechanical applicator positioning means coupled to the electromagnetic energy applicators for selectively positioning each of the plurality of applicators in the selected applicator receiving sites.

13. An apparatus for hyperthermic treatment comprising:
a flexible support means for providing good thermal contact with a contoured tissue surface;
a power distribution means for distributing power having a preselected amplitude and phase;
an array of electromagnetic energy applicators adjustably mounted in the support means and electrically connected to the power distribution means for controlling the distribution of heat in a tissue target having areas of varying power absorption and cooling; and
applicator adjustment means for selectively adjusting the positions of the applicators within the flexible support means.

14. An apparatus for hyperthermic treatment according to claim 13, wherein the applicators adjustment means is an electromechanical applicator positioning means coupled to the electromagnetic energy applicators for selectively positioning each applicator of the array of applicators in the flexible support means.

15. An apparatus for hyperthermic treatment, comprising:
a plurality of electromagnetic energy applicators;
a power distribution means for distributing electromagnetic power to the plurality of electromagnetic energy applicators;
a flexible, plastic bag;
a dielectric fluid contained within the bag, said dielectric fluid having a dielectric constant of at least two, whereby the bag and dielectric fluid therein will provide good thermal contact with a contoured tissue surface when the bag is placed against such contoured tissue surface; and
a plurality of applicator receiving tubes formed in association with the plastic bag, each receiving tube being configured to receive at least one electromagnetic energy applicator therein whereby the plurality of electromagnetic energy applicators are positioned in selected receiving tubes to form an array of electromagnetic energy applicators to provide electromagnetic energy through the dielectric fluid to a tissue target to heat such tissue target.

16. An apparatus for hyperthermic treatment according to claim 15, wherein the plastic bag is transparent to allow viewing of the surface of the tissue over which the bag is placed.

17. An apparatus for hyperthermic treatment according to claim 15, additionally including fastening means for fastening the bag over a tissue surface.

18. An apparatus for hyperthermic treatment according to claim 15, wherein each of the electromagnetic energy applicators have an active heating length, and the length of each receiving tube is sufficiently long to receive the entire active heating length of an electromagnetic energy applicator positioned therein.

19. An apparatus for hyperthermic treatment according to claim 15, additionally including means for individually adjusting the positions of the electromagnetic energy applicators within respective receiving tubes.

20. An apparatus for hyperthermic treatment according to claim 15, wherein the respective applicator receiving tubes are parallel to one-another.

21. Electromagnetic energy applicator supporting apparatus, comprising:
a flexible support means providing good thermal contact with contoured tissue surface when the support means is placed against such contoured tissue surface; and 'a plurality of applicator receiving sites formed in association with the support means, each applicator receiving site being configured to receive and hold at least one electromagnetic energy applicator, whereby the plurality of electromagnetic energy applicators are positioned at selected receiving sites to form an array of electromagnetic energy applicators to provide electromagnetic energy through the flexible support means to a tissue target to heat such tissue target.

22. The electromagnetic energy applicator supporting apparatus according to claim 21, wherein the flexible support means includes a flexible, plastic bag, and a fluid within the bag, whereby the bag and fluid therein will provide good thermal contact with a contoured tissue surface when the bag is placed against such contoured tissue surface, and wherein each applicator receiving site is a receiving tube formed in association with the plastic bag and configured to receive at least one electromagnetic energy applicator therein.

* * * * *